US008672941B2

(12) United States Patent
Bradica et al.

(10) Patent No.: US 8,672,941 B2
(45) Date of Patent: Mar. 18, 2014

(54) CORING DEVICE FOR PRESERVING LIVING TISSUE

(75) Inventors: Gino Bradica, Ewing, NJ (US); Timothy A. Ringeisen, Exton, PA (US)

(73) Assignee: Kensey Nash BVF Technology LLC, Wilmington, DE (US)

( * ) Notice: Subject to any disclaimer, the term of this patent is extended or adjusted under 35 U.S.C. 154(b) by 1733 days.

(21) Appl. No.: 11/049,410

(22) Filed: Feb. 2, 2005

(65) Prior Publication Data
US 2006/0173476 A1    Aug. 3, 2006

(51) Int. Cl.
*A61B 17/00*    (2006.01)

(52) U.S. Cl.
USPC .......................................................... 606/79

(58) Field of Classification Search
USPC ..................................... 606/95–98, 80–89, 79
See application file for complete search history.

(56) References Cited

U.S. PATENT DOCUMENTS

| | | | |
|---|---|---|---|
| 3,577,979 A * | 5/1971 | van der Gaast | 600/567 |
| 3,609,056 A | 9/1971 | Hougen | |
| 3,628,524 A | 12/1971 | Jamshidi | |
| 3,850,158 A | 11/1974 | Elias et al. | |
| 3,990,453 A * | 11/1976 | Douvas et al. | 606/107 |
| 4,142,517 A | 3/1979 | Stavropoulos et al. | |
| 4,491,124 A * | 1/1985 | Goettel | 126/293 |
| 4,649,918 A | 3/1987 | Pegg et al. | |
| 4,782,833 A | 11/1988 | Einhorn et al. | |
| 4,913,143 A | 4/1990 | Oloff et al. | |
| 5,324,300 A | 6/1994 | Elias et al. | |
| 5,423,823 A | 6/1995 | Schmieding | |
| 5,613,972 A * | 3/1997 | Lee et al. | 606/107 |
| 5,697,935 A | 12/1997 | Moran et al. | |
| 5,782,835 A | 7/1998 | Hart et al. | |
| 5,807,277 A | 9/1998 | Swaim | |
| 5,919,196 A | 7/1999 | Bobic et al. | |
| 5,947,989 A | 9/1999 | Shikhman et al. | |
| 6,007,496 A | 12/1999 | Brannon | |
| 6,139,562 A | 10/2000 | Mauze et al. | |
| 6,159,210 A | 12/2000 | Voor | |
| 6,398,793 B1 | 6/2002 | McGuire | |
| 6,488,033 B1 | 12/2002 | Cerundolo | |
| 6,592,588 B1 * | 7/2003 | Bobic et al. | 606/79 |
| 6,638,152 B1 | 10/2003 | Kim et al. | |

(Continued)

FOREIGN PATENT DOCUMENTS

EP    0141536    5/1985

OTHER PUBLICATIONS

Evans, Peter J., et al., "Manual Punch Versus Power Harvesting of Osteochondral Grafts", *Arthoscopy*, 20(3), (Mar. 2004),306-310.

(Continued)

*Primary Examiner* — Sameh Boles
(74) *Attorney, Agent, or Firm* — Jeffrey R. Ramberg

(57) ABSTRACT

Improved coring devices suitable for articular cartilage and bone, wherein the cutting device is capable of slicing through a tough protective tangential zone, delicately separating the shock absorbing columns of cells in the radial zone of the cartilage, and finally cutting into the hard underlying bone in a manner that preserves the viability of osteochondral cells. The coring device features an annulus having a flat annular cutting edge interrupted by at least one serration having neutral cutting angles. A method for concurrently removing cartilaginous and bony tissue using an improved coring device that preserves the viability of osteochondral cells.

19 Claims, 4 Drawing Sheets

(56) References Cited

U.S. PATENT DOCUMENTS

| | | |
|---|---|---|
| 6,767,354 B2 | 7/2004 | Johanson et al. |
| 2001/0034534 A1* | 10/2001 | Transue ........................ 606/186 |
| 2002/0042581 A1 | 4/2002 | Cervi |
| 2002/0157676 A1 | 10/2002 | Schmieding |
| 2003/0012844 A1 | 1/2003 | Starkey |
| 2003/0082797 A1 | 5/2003 | Rastorgoueff et al. |
| 2003/0199879 A1* | 10/2003 | Spranza, III ..................... 606/79 |
| 2004/0243136 A1* | 12/2004 | Gupta et al. .................... 606/82 |

OTHER PUBLICATIONS

Firoozbakhsh, PHD, K., et al., "Heat Generation During Ulnar Osteotomy With Microsagittal Saw Blades", *Iowa Orthopedic J*, 46-50.

Ovid, Natali „*J Bone Joint Surg Br*, 78-B(3), (May 1996).

Toksvig-Larsen, Soren, "Temperature Influence in Differenct Orthopaedic Saw Blades", *J Arthroplasty*, 7(1), (Mar. 1992),21-24.

\* cited by examiner

CORING DEVICE FOR PRESERVING LIVING TISSUE

BACKGROUND OF THE INVENTION

This application relates generally to medical instruments and methods of use for surgery and tissue excision, specifically relating to the removal of cartilaginous and bony tissue. A preferred embodiment more particularly concerns a device useful for preventing tissue damage and cell necrosis during a coring procedure in cartilaginous and bony tissue.

It is well known to utilize a hollow, annular drill bit, such as a trephine cutter, to cut into hard tissue, especially bone, as has been well documented in the prior art. For example, U.S. Pat. Nos. 3,609,056; 4,142,517; 4,782,833; 5,324,300; 5,423,823; 5,697,935; and 6,488,033, all describe annular cutting devices with saw teeth. Frequently, these devices are utilized in combination with either high speed drilling, axially impacting with a mallet, or a combination of both. Devices used in such a manner are not consistent with preserving cell viability in the affected tissue areas, as will be discussed below.

It is also well known to utilize coring devices, such as trephine cutters, to penetrate both soft and hard tissues (e.g., cartilage and bone, respectively) such as may be required in an osteoarticular transfer system (OATS) procedure. Osteoarticular transfer system (OATS) is a surgical method of repairing articular cartilage defects with hyaline cartilage. Limitations of the technique include the inability to deal with large and deep osteochondral defects, limited availability and possible damage to donor sites, non-filled spaces between the circular grafts and incomplete integration of the donor and recipient cartilage. The process for creating a plug or core typically results in an unfavorable level of cell necrosis. The instruments and techniques utilized in the practice of such a procedure may have considerable effect in minimizing the possible damage to the donor sites and thereby encouraging the integration of donor and recipient cartilage.

Historically, prior art devices have focused on the mechanics of cutting into tissues as if they were monolithic inanimate materials. In fact, tissues are living responsive populations of cells that have organized themselves, along with their extracellular matrices (e.g. proteins, glycosaminoglycans, etc.) into complex multiphasic architectural structures. These multiphasic structures have evolved to provide unique biologic and mechanical characteristics to the various tissues (e.g. bone, cartilage, skin, ligament, etc.). In particular, articular cartilage is one of the most micro-architecturally complex tissues in the body, as it features organized structure, instantaneously (i.e. not gradually) transitioning from a tangential orientation to a radial orientation, which then seamlessly flows into a calcified region, forming the osteochondral bond, and finally ending in subchondral cancellous bone. For these reasons, articular cartilage is a difficult tissue to repair. Adding even more complexity is the fact that that the subchondral bone region is an oxygen rich, high cell population, highly vascularized region (e.g., micro-vasculature) that is juxtaposed to an avascular, low cell population, low oxygen zone.

It has long been recognized in orthopedic operations that excess heat derived from drilling results may result in thermal injury and/or necrosis of nearby tissues. It is theorized the injury or necrosis may result from the denaturation of key enzymes required by the bone tissue, thermal damage to the cellular membrane, or the mechanical reorientation of collagen molecules upon exposure to elevated temperatures. Natali et al. describe a study of various bit designs for orthopedic use, measuring temperature increases as the drilling is performed in cortical bone. Elevated temperatures, even for relatively brief periods are capable of causing cell death. Microscopic studies of living bone tissue have shown a high sensitivity to heat stress, for example, Firoozbahsh et al. cited research reporting on the exposure of bone tissue to a temperature of 47 C for one minute, noting the effect of severely impaired bone regeneration.

Drilling designs for bone surgery devices have been incorporated into medical devices, especially trephine cutters. These types of devices using high speed drilling generate excessive heat due to friction between the blade and the material. Furthermore, research has shown that powered trephine devices, when utilized for cartilage grafting, frequently cause gross damage, such as shredding the soft tissue adjacent the bone, creating ragged graft edges, and possibly separating the cartilage from the subchondral bone. These ragged edges are indicative of the damage to which the cartilage tissue has suffered. Damage to this intricately oriented cartilage tissue, whether structural or mechanical, alters the tissue's ability to transmit loads. The creation of these ragged edges, architecturally affects the tissues ability to transmit the forces generated, for example during gait, and therefore increases the localized forces the surrounding cells are exposed to, leading to cell necrosis. Further study of these ragged edges demonstrate decreased cell viability, as the structure of the cells may be damaged.

In addition to the effects of thermal necrosis, and physical trauma (e.g., gross damage to tissue architecture), there is the potential for pressure necrosis when utilizing trephine cutters known in the art. For example, as described in U.S. Pat. Nos. 5,919,196 and 6,592,588, the coring tool or cutting tool is driven into the tissue by a mallet, which, upon impact forces the tool to penetrate the bone. The impacting force generates extreme localized pressure, which can cause pressure necrosis (physical damage to the cell) or injury of the surrounding tissues. Pressure necrosis in bone tissue may occur as cells exposed to a rapid pressure change (e.g., hammer blows, etc.) are injured (e.g. lysed, ruptured, etc.) as a result of the pressure change. The damage may occur in rigid tissue, as bone cells are injured by high forces, though it is believed that the rigid structure of bone would offer some protection to bone cells adjacent to the impacted area. The damage to adjacent non-rigid tissue may be more widespread than that of rigid tissue, as, with a non-rigid tissue (e.g. cartilage) the pressure force may be transmitted further by the non-rigid tissue as the soft tissue is displaced and deformed, rather than shielding the cells.

The prior art (for example U.S. Pat. Nos. 3,577,979; 4,649,918; 5,782,835; 6,007,496; and 6,767,354) describes annular cutting edges where one side of the cutting edge (whether an inside wall or outside wall) is vertical, and the other side has been sharpened, machined or manufactured to create a sharp blade. These designs, while they may be used for rigid tissue, suffer from a tendency for the edge to fold over, creating a dull edge. As the edge folds over, dulling the cutting blade, the potential for damage increases as greater friction and gross damage occur to soft tissue or hard tissue to which the tool is applied. Accordingly there is a need for a cutting surface that does not tend to fold over when applied against rigid tissue such as bone, preserving the original sharpness of the blade and therefore minimizing damage to osteochondral cells.

Johanson et al. in U.S. Pat. No. 6,767,354 describe a bone implantation apparatus featuring a harvesting tube and a cutting sheath which are arranged to harvest a bone plug from a donor site, and implant the plug into a prepared implant site. Johanson et al. describe preparing the implant site and the recipient hole for receiving the plug by means of applying a drill bit through a drill guide applied against the surface of the implant site, potentially causing gross damage as the hole is created. Johanson et al. do not describe a cutting tool having serrations to more easily penetrate bony tissue with his device when rotated, as the smooth cutting surface he describes would merely skate over the hard surface when rotated, thereby increasing the chance of damaging adjacent soft tissues. Johanson et al. describe an orthogonally extending tooth, penetrating into the inside bore of the device, which upon being driven, would create a channel in the core plug as the device is driven into the hard tissue. Upon reaching an appropriate depth of penetration, the tip is rotated, such that the tooth causes the plug of material to be severed at the base of the plug.

Spranza in U.S. Patent Application Publication No. 20030199879 describes a bone coring device that is fabricated with a cutting end having a thicker section wall at its distal surface to be placed against tissue, and narrowing towards the proximal end of the tooth, in order to minimize friction between the shank of the device and the adjacent tissue. This thicker cutting end makes the device unsuitable for cutting soft tissues, as the increased width of the cutting edge will impact a large area of soft tissue, and generate a wider swath of gross damage. In order to penetrate harder tissues, a great deal of axial pressure will be required as the force is distributed over a thicker cutting edge than would be the case with a sharper knife-edged coring device. The device described by Spranza requires application of a uni-directional cutting force in order for the tool to be effective.

There exists a need for coring tools useful for articular cartilage wherein the cutting devices are capable of slicing through the tough protective tangential zone, delicately separating the shock absorbing columns of cells in the radial zone and finally cutting into the hard underlying bone. All this must be done in a way that preserves the limited cell population in the cartilage zone; prevents excessive tissue debris that attracts macrophages that could release or stimulate angiogenic factors in the cartilage region causing it to calcify; and still preserves the micro-vasculature of the subchondral bone. To the best of applicants' knowledge, no prior art has combined these aspects into a unique single cutting tool that is sympathetic to both the multiphasic micro-architectural characteristics of the tissue and the biologic requirements of the cell populations which exist in those architectures.

The prior art described does not disclose a device suitable for coring a combination of soft and rigid tissues, while adequately preserving cell viability. It is the intent of this invention to overcome the shortcomings of the prior art in creating a coring tool having features that minimize the occurrence of cell necrosis, preserves cell viability in coring both soft and rigid tissues and in some embodiments is strong enough to allow repeat usage.

SUMMARY OF THE INVENTION

The following are a non-exhaustive list of objects of the present invention.

It is a purpose of the current invention to provide a novel, multiphasic cutting tool capable of:
- easily cutting through the tough tangential zone of articular cartilage with a level cutting edge;
- carefully separating the columns of cell within the radial zone with minimal tissue debris using a double beveled wedge/chisel edge; and
- easily cutting into hard calcified subchondral bone with a neutral angle serration.

It is an object of this invention to provide a coring device which preserves cell viability of affected tissue, that is, tissue within and adjacent the coring device while in use.

It is another object of the invention to provide for preservation of cell viability by utilizing techniques for coring tissue that minimize such generating of excessive heat or pressure that would result in heat or pressure necrosis.

It is another object of the invention to create a coring device that is easier to use than is a powered coring device, which has a more frequent occurrence of inadvertent skidding across the bone surface.

It is another object of the invention to remove a core or plug of tissue leaving an opening of precise dimensions, such that a known plug size may be inserted into said opening.

It is another object of the invention to create a strong tool, capable of repeated use without losing its edge or fracturing while in use.

These and other objects of this invention may be achieved by providing a coring device for penetrating both hard and soft tissues in a living being. The device is able to penetrate into hard tissue such as bone, and soft tissue such as cartilage, and preserve the cell viability of osteochondral cells. The device features an annular cutting element at the distal end of the tool, which is made up of alternating level cutting edges and serrations. The serrations have neutral cutting angles providing a cutting tip arranged so as to prevent causing significant soft tissue damage, yet provide the ability to penetrate into bony tissue without requiring excessive pressure or speed, which might otherwise lead to loss of cell viability. The serrations feature a radius curve portion between the neutral angles to prevent fracture, especially spiral fractures of the tool. The level cutting edges are formed in the center of the thickness of the tubular wall of the cutting area of the head, thereby presenting a strong cutting edge to the tissues, as it is equally supported on both sides. The device may be coated in order to enhance its properties.

DETAILED DESCRIPTION OF PREFERRED EMBODIMENTS

The present invention provides devices and methods for coring tissue of exact dimensions, wherein the viability of the cells in the tissue is substantially preserved. It has surprisingly been found that to facilitate effective integration of an implanted osteochondral core plug, not only must the osteochondral cell viability of the core plug material be preserved, but further the osteochondral cell viability of the surrounding tissue ought to also be preserved. In this manner, a plug of living material is able to be integrated into a surrounding area of living material. The present invention utilizes low speed, low impact techniques to neatly slice through soft tissue, such as cartilage, dividing the soft tissue with a cutting element having a sharpened level cutting edge surface, and preserving the viability of soft tissue cells. The present invention is also capable of cutting into to rigid tissue, such as bone, as the cutting element also features a plurality of serrations having neutral cutting angles and providing cutting tips, which may penetrate and divide rigid tissue, without generating excessive heat or pressure. The term cutting tip may be interchangeable with the terms cutting surface or cutting face, and includes the cutting portion of the serration of the cutting element. It has been found that the serrations featuring neutral cutting angles are able to be utilized for soft tissue division without significantly affecting osteochondral cell viability. Additionally, the serrations having neutral cutting angles and a radius curve are able to penetrate into bone and do not create stress points which tend to cause fracture of the device. The necessity to strengthen the instruments cutting edge by eliminating stress points becomes more evident when minimizing wall thickness which may serve to minimize the area of affected cells, but at the expense of removing added material strength. Furthermore, the present invention provides for a level cutting edge that resists deformation, thereby lengthening the usable life of the tool.

The following description describes the device assembly, components and features depicted in the figures, wherein like numbers refer to like components.

Figure 1:
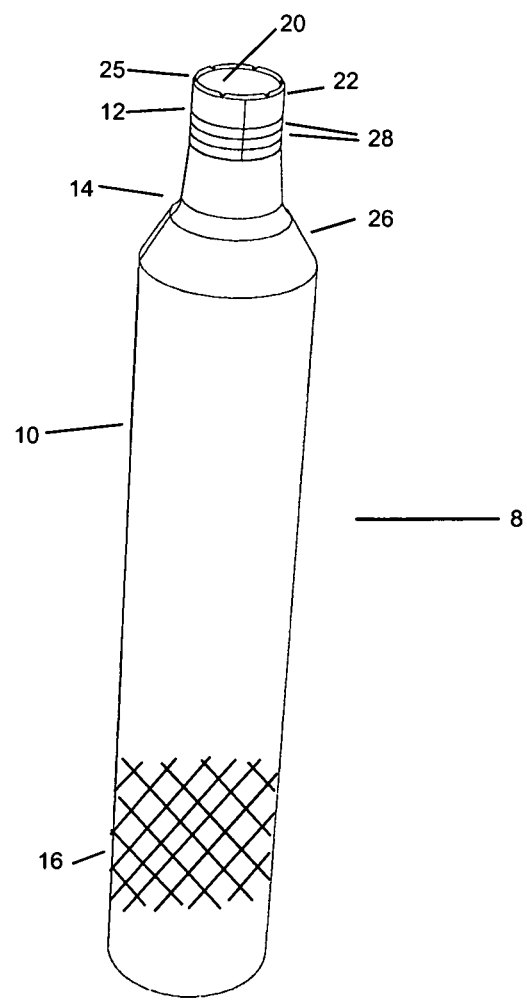
FIG. 1 An elevated profile view of the coring device.

With reference to FIG. 1, one embodiment of the coring tool 8 is depicted. A coring tool, in accordance with this invention, generally has at least the following components, a body 10, a head or tip 12, and a neck 14 arranged between the body and head. The body, as depicted here, may have a handle section 16 arranged for gripping the coring tool while in use. Alternatively the body may be capable of accepting, receiving, or otherwise being affixed to a handle, as will be discussed below. The head 12 of the coring tool 8, may be in the form of an annulus located at the distal end of the coring tool. This annulus is a hollow cylindrical section having an inner wall 20 and an outer wall 22, between them defining a wall thickness. The annulus may be of substantially uniform outside diameter over its length, albeit with a cutting edge 24 at the distal end of the annulus. The proximal end of the annulus is attached to the neck 14 of the coring tool 8. It is recognized that the body 10 and neck 14, may be solid or hollow, or a combination thereof. In an entirely hollow embodiment of the coring tool 8, the inner wall 20 may form an internal surface defining an internal bore extending along the longitudinal axis from the distal end of the device (at the cutting element), through to the proximal end of the device (through the body and/or handle).

A cutting element 25 may be provided at the distal end of the annulus and may be arranged for cutting into soft tissue, rigid tissue, or a combination of both (as will be described below). The neck 14 portion may be arranged between the proximal surface of the head 12, and the body 10, such that the neck varies in outside diameter (e.g. tapered, terraced, etc.) such that a transition between the body 10 and head 12 diameters is created.

In one embodiment, the device 8 comprises a separate handle (not shown), to which may be fastened a variety of devices. In this manner, a particular coring device may be utilized for a particular situation; for example, various sizes of cores may be created by utilizing a specifically sized coring device. The handle may be formed to allow the user to grip and apply proper torquing forces, and may have a variety of shapes, including but not limited to a T-shaped handle, and L-shaped handle, or others known in the art. Additionally, the handle may be a knurled section, or tubular extension, or other known gripping area known in the art. In another embodiment, the handle 16 is formed as an integral part of the coring device 8 (as shown in FIG. 1), and is not separable, though it may be shaped in any of the manners contemplated above.

It is recognized that the handle 16 may incorporate a ratcheting or gear mechanism (not shown) to allow operation of the coring tool 8 in one direction, and resetting of the handle back to the original orientation without the need for the surgeon to release his grasp. In another embodiment, the coring tool 8 is capable of operation regardless of the direction of the twisting force applied, as will be discussed with reference to the cutting surfaces below.

The neck 14 portion of the device serves to transmit forces applied to the body or handle 16, down to the distal end of the coring device through the head. The neck portion also serves to transition the diameter of the device 8 between the body 10 and the head 12, and allow penetration into and visibility of targeted tissue, without interference from the larger diameter of the body 10 or handle 16. In one embodiment, the neck 14 may feature a taper or series of tapered sections 26 that accomplish the sought diameter reduction between the head and the body. The neck portion should be sufficiently strong to withstand both torquing and axial forces without breaking as the device is employed. A neck 14 featuring at least a portion of the outside diameter being tapered may be able to dissipate the stress of the expected forces, and minimize the potential for tool fracture. It is recognized that the coring tool 8 may feature various markings for alignment and measurement, for example, in an embodiment, the neck portion 14 may have markings 28 to indicate depth of penetration into tissue.

Figure 2:
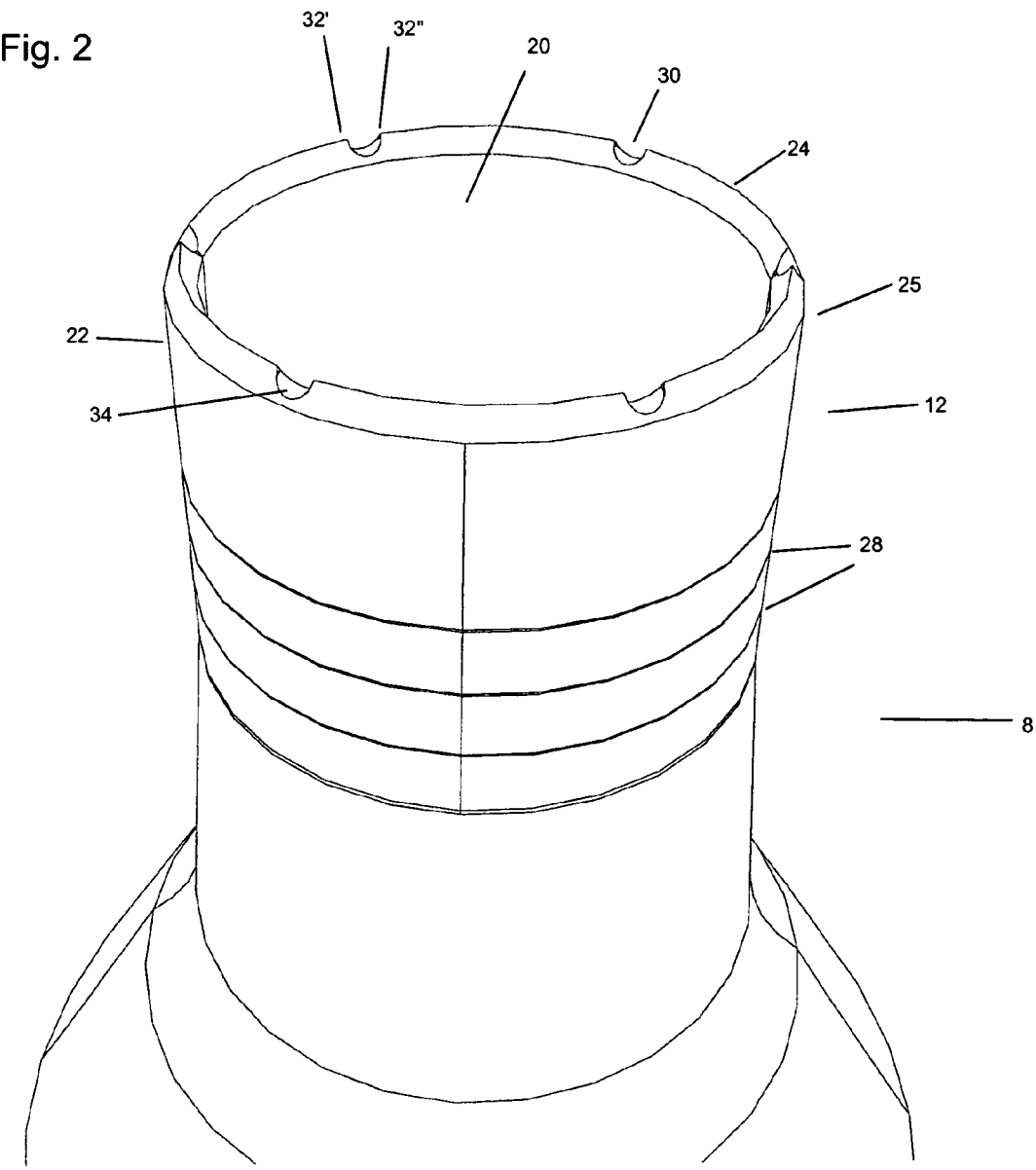
FIG. 2 An enlarged view of the distal end of the coring device of the present invention.

With reference to FIG. 2, there is depicted an expanded detailed view of the head 12 of one embodiment of the present invention. The head, as depicted here features a tubular wall construction created between an inner wall 20 and outer wall 22. The tubular wall forms an annulus having a cutting element 25 at the distal end of the annulus. The cutting element is composed of a combination of level cutting edge 24, and at least one serration 30. The cutting edge 24 may be created by various means, for example by a double honed surface, such that the resulting annular cutting edge 24 is roughly centered between the inner wall 20 and outer wall 22 within the thickness of the tubular wall of the annulus. This is in contrast with prior art designs where only a single honing process was utilized, and the cutting edge remains skewed to one side of the cutting tube, and favoring either the inner wall or the outer wall of the prior art having an annular cutting edge. The drawback with the prior art single honed cutting designs is the lack of strength necessary for cutting hard tissues, such as bone. In practice of this prior art, the sharp cutting edge would tend to fold over due to lack of wall thickness as cutting pressure is applied against hard tissue. This results in a dulling of the cutting edge, resulting in increased friction and associated heat generation, as well as increased damage to nearby cells with a reduction in cell viability as a result of continued use of the prior art designs. The design of the present invention maintains an enhanced wall thickness to prevent the folding over and resultant dulling of the cutting edge 24, furthermore, there is a reduced tendency for the cutting edge to fold over in response to cutting pressure as the pressure is evenly distributed on both sides of the cutting edge as the encountered forces are dissipated by being transmitted through to both the inner wall 20 and outer wall 22 evenly.

An additional benefit of the centered cutting edge 24 of the present invention is the extent to which tissue is compressed as the device is advanced further into target tissue. With prior art designs featuring single hone features (where the cutting edge is skewed either to the inside or outside of the cutting tube), the tissue is compressed entirely in one direction, for a distance equal to roughly the width of the tubular wall comprising the coring device. In contrast, the double hone design of the centered level cutting surface 24 of the present invention allows the compression to occur in two directions as the tissue is split, and only for a distance roughly equal to one half of the width of the tubular wall of the annulus of the head 12. This minimizes the extent to which compression is required, and facilitates the insertion of the device further into the tissue, and concurrently minimizes the potential for tissue damage or reduced cell viability.

The cutting element 25 of the head 12 of the coring device 8 is largely a level cutting edge 24, interspersed with serrations 30, so the cutting element 25 may neatly split the soft tissue, slicing through with minimal damage, evidence by tearing or shredding of the soft tissue, thereby preserving cell viability in the soft tissue (e.g. chondrocytes). The prior art devices having only a level cutting surface, upon slicing through soft tissue, and arriving upon rigid tissue (e.g., bone) would be unable to slice through, and instead would skate over the hard surface without making any real purchase into the depth of the rigid material. While this prior art device is being rotated against hard tissue without purchase, there tool may move laterally, and resulting in a loss of osteochondral tissue viability as the edge tears at the soft tissue or otherwise distorts the soft tissue. It has been noted that in order for the cutting edge to penetrate into hard tissue, there should be some method of allowing the edge to gain purchase on the hard tissue. It has been noted that providing a plurality of serrations will allow the level surfaces to gain purchase. The serrations are concave; that is, they are proximally directed and represent regions where annulus material has been removed to form indentations. As such, the serrations provide an opening for debris that is generated to accumulate, and prevent binding of the cutting edge in the hard material. Other devices featuring serrated edges at non-neutral angles (such as a saw tooth design, or inverted saw tooth design) were observed to cause shredding of the soft tissue and therefore loss of cell viability, as the device was rotated. It has surprisingly been found that a coring device having an annular cutting element 25 having the aforementioned level cutting edge 24 and incorporating a plurality of serrations 30 with neutral cutting angles 32' and 32", interspersed between the level sections, serves to neatly cut and core into both soft and hard tissues, while preserving the cell viability of the respective tissues.

In practice of the present invention, it has been found that the cutting element having a level cutting edge 24 may enable the cutting tool to be capable of slicing through the tough protective tangential zone in a multiphasic architectural structure or tissue, such as osteochondral tissue. Furthermore, the cutting edge being made central to the wall thickness of the annular ring may serve to delicately separate the shock absorbing columns of cells in the radial zone, for example, by minimizing the amount of compression in a lateral direction. The cutting tool featuring a plurality of serrations 30 may be made capable of cutting into the hard underlying bone, where the serrations featuring nearly neutral or neutral cutting angles (32' and 32") do not serve to destroy the cells' viability, as would more likely occur with a non-neutral cutting angle. All these features may assist in the preservation of the limited osteochondral cell population in the cartilage zone; thereby preventing excessive tissue debris that attracts macrophages that could release or stimulate angiogenic factors in the cartilage region causing it to calcify; and still preserves the micro-vasculature of the subchondral bone.

Figure 3A:
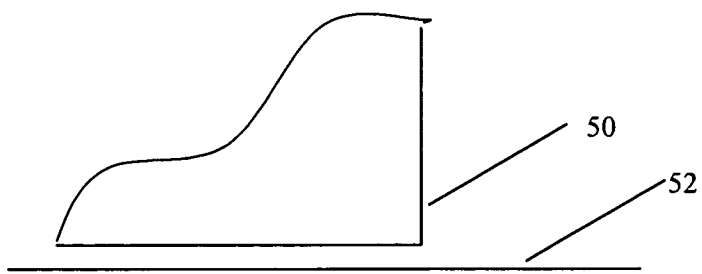
FIGS. 3A-C Example depictions of neutral, positive and negative cutting angles, respectively.
Figure 3B:
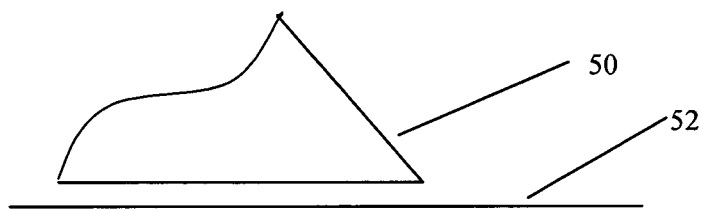
Figure 3C:
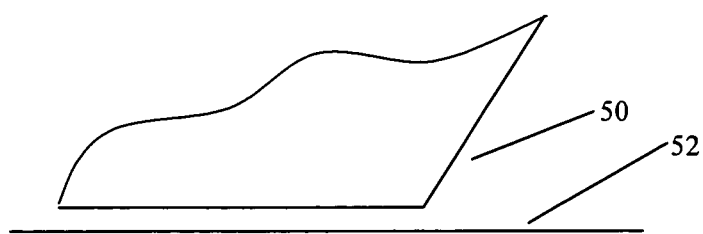

The serrations 30 created in the annular cutting edge 24 are created having a pair of neutral cutting angles 32' and 32", or minor variations from a neutral cutting angle. A neutral cutting angle is created where, at the interface of the serration and the flat section of the annular cutting edge, there is a 90° angle, as depicted by the tooth 50 shown in FIG. 3A. In contrast, positive and negative cutting angles are created when there is variation from the neutral cutting angle. For illustration of these non-neutral cutting angles, FIG. 3B depicts a tooth 50 having a positive cutting angle and FIG. 3C depicts a tooth 50 having a negative cutting angle, where the movement of the cutting tooth 50 occurs from left to right, and where the cutting angle is measured between the surface doing the cutting and the surface of the tissue substrate 52 or material being cut ahead of the tooth. In practice, a positive cutting angle is a more aggressive cutting angle, and there is more of a tendency for the cutting tip to grab the tissue being cut; while a negative cutting angle is less aggressive, and there is a tendency for the cutting tip to slide across the tissue without having much effect on tissue, unless large axial loads are applied. A positive cutting angle will more likely fracture upon hitting a hard tissue such as bone. This is because a stress point is created where energy is stored, and eventually shatters the material of the device, or allows deformation if the material of the device is too soft. The lead cutting edge of the cutting surface in a positive cutting angle is weaker due to the reduced material present, which increases the probability for fracture and the potential for debris from shattered device being left in tissue. A negative cutting angle may not be suitable for cutting hard tissue as it may not be aggressive enough in cutting, and will require more applied axial force in order to cut into more dense tissue, such as bone, potentially leading to increased tissue and cell damage when cutting forces are applied.

In a preferred embodiment, the serration 30 is not in the form of a sawtooth, but rather has left-right symmetry. Each serration forms a pair of cutting tips at cutting angles 32' and 32", wherein the cutting tips include vertical or near vertical cutting portions of the serration 30 that intersect with the horizontal portion of the cutting edge 24. However, in regular use of the coring tool 8 only one cutting tip of the pair of cutting angles 32' and 32" is engaged in cutting at a time. For instance, when a serration is moving from left to right across a surface to be cut, the cutting surface on the left side of the serration is engaged, and the cutting surface on the right side of the serration is idle, since the material to be cut is moving in a direction that is away from that cutting surface. Though it is recognized that for soft tissues, there may be an opportunity for the soft tissue to fill the space created by the concave serration, and be exposed to the cutting surface that would otherwise be idle if applied against rigid tissue. The cutting angle is the angle that may be measured between the surface of the material to be cut and the cutting surface of the left side of the serration adjacent to the level cutting surface. Similarly, when the direction of rotation is reversed, the left cutting surface is idled, and the right cutting surface of the serration becomes engaged in cutting. Again, the cutting angle is the angle that may be measured between the surface of the material to be cut and the cutting surface of the right side of the serration adjacent to the level cutting surface. But since the serration has left-right symmetry, these angles are the same. Consequently, the coring device of the present invention is capable of being rotated in alternating directions with equal cutting efficiency. The reversibility does not depend on the precise cutting angle, just that they are the same. Nevertheless, an approximately neutral cutting angle is preferred, for reasons discussed previously.

In order to dissipate stress, or resist fracture of the device 8 as the hard tissue is cut, the present invention incorporates a radius curve 34 built into the serrations 30 between the walls formed by the neutral cutting angle 32, as can be seen in FIG. 2. The radius curve 34 aids in creating a more uniform stress distribution, as the size of the radius creates more surface area for the stress to be distributed across. In contrast to prior art serrations featuring an acute angle (i.e. a sawtoothed pattern), a radius curve prevents fracture of the cutting device when applied against hard tissue, as the stresses do not tend to accumulate at a stress point created at the sharp corner of the sawtoothed device. The radius curve portion 34 may be a scalloped edge that does not include a sharpened cutting surface, or in another embodiment, the scalloped edge may further be sharpened, or honed similarly to the cutting edge 24, in order to create a secondary cutting edge within the serrated portion. Alternatively, and as depicted in FIG. 2, the radius curve may feature a scalloped but largely uniformly curved surface that is flat in a direction orthogonal to the curve, wherein the width of the surface matches of the thickness of that portion of the annular wall.

Figure 4A:
FIG. 4A Photomicrograph of tissue sample showing viability and integration of cellular materials when coring procedure is performed with prior art coring device.
Figure 4B:
FIG. 4B Photomicrograph of tissue sample showing viability and integration of cellular materials when coring procedure is performed with device of the present invention.

FIGS. 4A and 4B are the photomicrographs depicting the histology results of a pair of osteochondral coring procedures. In FIG. 4A, a device lacking the features of the present invention as described was utilized for the coring, and in FIG. 4B, the device of the present invention was utilized. For this study, two, 24-week, samples were explanted from a New Zealand White Rabbit medial-distal femoral condyle. The defect in FIG. 4A was created with a coring tool lacking the neutral cutting angles of the present invention and featured a smooth cutting edge only, manufactured through a single hone process, such that the cutting edge was skewed towards the inner diameter wall of the device. The defect in FIG. 4B was created with an embodiment of the coring tool 8 of the present invention, having a centered cutting edge, with a plurality of serrations featuring neutral cutting angles and a radius curve. Both defects created and depicted in FIGS. 4A and 4B were filled with a biphasic osteochondral implant material saturated with saline solution at time of surgery. The tissue samples were stained with Safranin-O stain to identify proteoglycans (depicted here with the dark colored stain) and cell nuclei (depicted here as small black granules). A decreased proteoglycan content serves as a biochemical marker that coincides with damage to the tissue or cartilage viability. Note in FIG. 4A there is poor integration to host tissue (evidenced by the visible gaps within the circled areas) and the lack of cell viability (due to the lack of dark staining within the circled areas) at the juncture between the core material and the adjacent surrounding host tissue. In FIG. 4B, there is no indication of lack of integration to host tissue, and the staining indicates a consistent and higher level of cell viability relative to FIG. 4A.

The coring device 8 of the present invention may be manufactured from a variety of materials or combinations of materials known in the art of surgical devices (e.g., stainless steel, ceramics, glass, titanium, plastics, polymers, etc.). It is recognized that any material capable of being used to penetrate tissue may be utilized, and it is also recognized that the present invention is able to utilize materials not compatible with coring devices requiring impacting axial forces (e.g., hammer blows) or high speed rotation and friction techniques (e.g., high speed drilling). In an embodiment, the device 8 may feature a coating applied to all or a portion of the surfaces of the coring device 8 which may serve to impart at least any or all of the following: enhanced lubricity, enhanced hardness, enhanced maintenance of cutting edge, enhanced resistance to damage to the device through cleaning and sterilization processes. The coating may be of various coatings known in the art, depending on the substrate material selected for manufacture of the device, including Titanium, Nickel, Nickel-Titanium, Diamond-Chromium, Chrome, PTFE polymer, etc. For example, a diamond-chromium coating may be applied to enhance the tool performance and function. A coating may improve performance by, among other aspects, serving to fill any imperfections in the base material of the device, or prevent contamination or reaction with foreign materials (e.g., cleaning agents, sterilizing agents, etc.)

In an embodiment, the coring tool is suitable for repeat usage, being capable of being cleaned, and sterilized between uses. In another embodiment, the entire device is disposable, and is suitable for single use. In still another embodiment, a portion of the device is disposable, and the portion suitable for repeat usage is able to be attached to a disposable portion by means known in the art (e.g., threaded bodies, clamps, interlocking components, etc.) For example, in a device featuring a disposable portion, or entirely disposable, it may be beneficial to fashion the disposable componentry from plastic, such that manufacturing costs and material costs are minimized. In this manner, the entire device may be manufactured from plastic, and the cutting element manufactured by means known in the art (e.g., casting, machining, milling, etc.) Alternatively, there may be benefit to providing a reusable handle portion 16, or body portion 10, and coupling that reusable portion with a disposable cutting element 25 or head 12.

In an embodiment, the interior surface 20 of the device 8 may not feature a polished surface (as is preferred for the exterior surface 22), but rather may be striated or rough in order to more effectively grip an introduced plug core, so that upon removal of the coring device from the living being after use, the tissue material within the device is removed concurrently. Alternatively, the inner diameter of the device may be smooth, and not feature any striations or markings on the internal wall. This ensures the device may penetrate into the tissue, and also serve to preserve the viability of the plug material, such that it may then be salvaged for use in a procedure (e.g., OATS procedure). A plug removed in this manner may be removed from the tool by the insertion of a pushing tool (e.g. a rod) down through the interior of the body and neck of the device, and may press the material out from the device. Alternatively, the use of vacuum or pressure may be utilized to drive the plug of material out of the device 8, and into a suitable receptacle, either for immediate implantation or preserved storage.

In an embodiment, the plug of tissue within the coring 8 device, while still remaining inserted into the living being, may be removed by inserting a drill bit (not shown) through an internal bore running through the length of the device 8, where the drill bit has a flat distal boring surface that may serve to create a perpendicular base in the core opening. Upon rotation of the drill bit, the fluting of the drill bit may serve to remove tissue freed by the boring rotation of the drill bit. In this manner, the coring device 8, also serves to protect the adjacent tissue from damage as the drill bit is operated. As with the coring device, care should be taken not to generate excessive heat that would hurt the viability of the osteochondral cells.

Alternatively, the coring device 8 may be removed, and a separate protective hollow sheath (not shown) similar in outside diameter to the head 12 of the coring device 8, may be placed within the core margin created by the device 8, such that the sheath may afford protection to nearby tissue as a drill bit is inserted as described above. Further, the sheath may serve to preserve alignment of the drill bit as it is being inserted.

In practice of the present invention, a surgical opening may be created at the target site. The target site may be an area having a combination of soft and hard tissue, such as osteochondral tissue featuring both cartilaginous and bony tissue. The tool may then be placed upon the target tissue, and rotated by the handle, without generating excessive heat and pressure. Excessive heat and pressure is an amount that would harm a substantial proportion of the osteochondral cells. This may be achieved through, for example, slow speed manual rotation, or low speed automated rotation. The direction of rotation may be unidirectional (i.e., clockwise or counter-clockwise only). Moreover, since each side of a symmetrical serration makes the same cutting angle with respect to the surface being cut when that side is engaged in cutting, there is no harm in reversing the direction of travel. Thus, the device may be operated in a counter-rotating manner. While being rotated, minimal force may be applied axially to drive the cutting edge through the soft tissue and hard tissue. It is recognized that increased axial force may be required to penetrate into hard tissue. In any event, the axial force applied should be maintained at a level that is unlikely to harm overall cell viability (as would sharp or large application of force, e.g., a hammer blow). The slicing action of the cutting edge divides the soft tissue, while the serrations having neutral cutting angles allow the device to penetrate hard tissue, until a desired depth is reached (which may be determined using markings 28 on the head 12), thereby creating a core plug of osteochondral material contained within the device.

In order to create a proper surface for receiving an implant of osteochondral material, the original material within the device may be removed along with the tool itself, or alternatively by application of a drill bit inserted through the length of the coring device. In another practice of the current invention, the tool may be removed after penetrating into the osteochondral tissue, and in its place a sheath inserted, through which a drill bit may be inserted.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. An improved tissue cutting device, comprising:
    (a) a head, a body, and a neck arranged between said body and said head;
    (b) wherein said head comprises a tissue cutting portion comprising an annulus comprising (i) a uniform outside diameter wall, and (ii) an annular cutting element on a distal surface of said annulus, said annular cutting element comprising at least one level surface interrupted by at least one proximally directed serration, said serration being defined by a radius curve, said at least one level surface having a sharp edge that is arranged to neatly slice soft tissue, wherein a junction of the level surface and the serration forms a pair of cutting angles, wherein said cutting angles are each arranged at or about a nearly neutral cutting angle;
    (c) wherein said body comprises a handle for gripping, said handle being integral with said tissue cutting portion and arranged to allow a user to apply proper torquing force to said tissue cutting portion; and
    (d) whereby said device is arranged to cut both soft tissue and hard tissue while preserving cell viability of adjacent tissue.

2. The device of claim 1, wherein said soft tissue comprises cartilage, said hard tissue comprises bone tissue, and said cell viability comprises viability of osteochondral cells.

3. The device of claim 1, further comprising a coating over at least a portion of the device.

4. The device of claim 3, wherein said coating is arranged to prevent tool erosion and wear.

5. The device of claim 3, wherein said coating is lubricious.

6. The device of claim 1, further comprising a body and a neck, wherein said body comprises a tubular body of larger diameter than said annulus, and wherein said neck is arranged between and joins said body and annulus.

7. The device of claim 1, wherein said radius curve comprises a sharp edge.

8. The device of claim 1, wherein said annular cutting element is arranged to be rotated by hand.

9. The device of claim 8, wherein said rotation is bi-directional.

10. The device of claim 1., wherein said serration has left-right symmetry.

11. An improved tissue cutting device, comprising a tissue cutting portion comprising an annulus having (i) an outside wall of uniform diameter, and (ii) an annular cutting element on a distal surface of said annulus. said annular cutting element comprising at least one level surface interrupted by at least one proximally directed serration, said serration being defined by a radius curve, said at least one level surface having a sharp edge that is arranged to neatly slice soft tissue, said at least one serration being arranged to cut into hard tissue, wherein a junction of the level surface and the serration forms a pair of cutting angles, wherein said cutting angles are each arranged at or about a nearly neutral cutting angle, wherein said device is arranged for manual rotation and whereby said device preserves cell viability.

12. The multiphasic cutting tool of claim 11, further comprising a means for supporting said tissue cutting portion.

13. The multiphasic cutting tool of claim 12, wherein said means for supporting said tissue cutting portion comprises at least a body portion arranged for providing a gripping area for said multiphasic cutting tool.

14. The multiphasic cutting tool of claim 12, wherein said means for supporting said head portion further comprises a neck portion, wherein said neck portion is arranged between said body portion and said head portion.

15. The multiphasic cutting tool of claim 12, further comprising a coating over at least a portion of the cutting tool.

16. The multiphasic cutting tool of claim 15, wherein said coating is arranged to prevent tool erosion and wear.

17. The multiphasic cutting tool of claim 15, wherein said coating is lubricious.

18. The multi-phasic cutting tool of claim 11, wherein said serration has left-right symmetry.

19. The multi-phasic cutting tool of claim 11, wherein said annular cutting element is arranged to be rotated such that, during said rotation, one of said pair of neutral cutting angles is active, and the other of said pair is idle.

* * * * *